US006887676B1

(12) United States Patent
Collinge et al.

(10) Patent No.: US 6,887,676 B1
(45) Date of Patent: May 3, 2005

(54) METHOD TO TYPE PRION PROTEINS (75) Inventors: John Collinge, London (GB); Jonathan David Frank Wadsworth, London (GB)

(73) Assignee: D-Gen Limited, London (GB)

(*) Notice: Subject to any disclaimer, the term of this patent is extended or adjusted under 35 U.S.C. 154(b) by 0 days.

(21) Appl. No.: 09/958,517

(22) PCT Filed: Apr. 7, 2000

(86) PCT No.: PCT/GB00/01327

§ 371 (c)(1),
(2), (4) Date: Feb. 12, 2002

(87) PCT Pub. No.: WO00/62068

PCT Pub. Date: Oct. 19, 2000

(30) Foreign Application Priority Data

Apr. 9, 1999 (GB) .............................................. 9908059

(51) Int. Cl.[7] .......................... C12Q 1/37; C12Q 1/00; C12N 9/48; C12N 9/50; C07K 14/00

(52) U.S. Cl. ........................... 435/23; 435/4; 435/184; 435/212; 435/219; 530/350; 530/400

(58) Field of Search .......................... 435/5, 7.1, 7.5, 435/7.9, 23, 7.92, 68.1, 69.1, 4, 183, 184, 212, 219; 424/183, 184, 185.1, 212, 219, 405; 422/28; 530/328, 350, 400, 403; 436/501

(56) References Cited

U.S. PATENT DOCUMENTS

| 5,891,641 A | 4/1999 | Prusiner et al. | |
|---|---|---|---|
| 6,214,366 B1 | * 4/2001 | Prusiner et al. | 424/405 |
| 6,617,119 B2 | * 9/2003 | Prusiner et al. | 435/7.1 |

FOREIGN PATENT DOCUMENTS

WO    WO 98 16834 A    4/1998

OTHER PUBLICATIONS

Medline, Washington DC USA; Abstract No. 20030576, whole abstract, XP002143073 & J.D. Wadsworth et al, "Strain–Specific Prion–Protein Conformation Determined by Metal Ions", Nature Cell Biology, vol. 1, No. 1, May 1, 1999, pp. 55–59, London UK.
"Release of endogenous $Zn^{2+}$ from brain tissue during activity", by S.Y. Assaf & Shin–Ho Chung, *Nature (Letters to Nature)*, vol. 308, Apr. 19, 1984, pp. 734–736.
"Dramatic Aggregation of Alzheimer Aβ by Cu(II) Is Induced by Conditions Representing Physiological Acidosis" by Craig S. Atwood, et al, *The Journal of Biological Chemistry*, vol. 273, No. 21, May 22, 1998, pp. 12817–12826.
"Distinct PrP Properties Suggest the Molecular Basis of Strain Variation in Transmissible Mink Encephalopathy" by Richard A. Bessen et al, *Journal of Virology*, vol. 68, No. 12, Dec. 1994, pp. 7859–7868.

"Non–genetic propagation of strain–specific properties of scrapie prion protein" by Richard A. Bessen et al, *Nature (Letters to Nature)*, vol. 375, Jun. 22, 1995, pp. 698–700.
"The cellular prior protein binds copper in vivo", by David R. Brown, et al, *Nature (Letters to Nature )*, vol. 390, 18/15 Dec. 1997, pp. 684–687.
"Prion protein expression and superoxide dismutase activity" by David R. Brown et al, *Biochem*, J. 334 (1998), pp. 423–429.
"Transmissions to mice indicate that 'new variant' CJD is caused by the BSE agent" by M.E. Bruce et al, *Nature (Letters to Nature)*, vol. 389, Oct. 2, 1997, pp. 498–501.
"Spongiform Encephalopathy Induced in Rats and Guinea Pigs by Cuprizone [1,2]" by William W. Carlton, *Experimental and Molecular Pathology* 10 (1969), pp. 274–287.
"Strain–dependent Differences in Beta–sheet Conformations of Abnormal Prion Protein" by Byron Caughey, et al, *The Journal of Biological Chemistry*, vol. 273, No. 48, Nov. 27, 1998, pp. 32230–32235.
Human prion diseases and bovine spongiform encepthalopathy (BSE) by John Collinge, *Human Molecular Genetics*, 1997, vol. 6, No. 10 Review, pp. 1699–1705.
"Genetic predisposition to iatrogenic Creutzfeldt–Jakob disease" by John Collinge, et al, *The Lancet*, vol. 337; Jun. 15, 1991, pp. 1441–1442.
"Prion Protein gene analysis in new variant cases of Creutzfeldt–Jakob disease" by John Collinge, et al, *The Lancet*, 1996.
"Molecular analysis of prion strain variation and the aetiology of 'new variant' CJD" by John Collinge, et al, *Nature*, vol. 383, Oct. 24, 1996, pp. 685–690.
"Surgical treatment and risk of sporadic Creutzfeldt–Jakob disease: a case–control study" by S. Collins, et al, *The Lancet*, vol. 353, Feb. 27, 1999, pp. 693–697.
"Stability constants of metal complexes" by Rex M.C. Dawson, et al, *Data for Biochemical Research*, Third Edition, 1986, pp. 399–415.
"The same prion strain causes vCJD and BSE" by Andrew F. Hill, et al, *Nature*, vol. 389, Oct. 2, 1997, pp. 448–450.
"Investigation of variant Creutzfeldt–Jakob disease and other human prion diseases with tonsil biopsy samples" A.F. Hill, et al, *The Lancet*, vol. 353, Jan. 16, 1999, pp. 183–188.
"Copper Binding to the N–Terminal Tandem Repeat Regions of Mammalian and Avian Prion Protein" by M.P. Hornshaw, et al, *Biochemical and Biophysical Research Communications*, vol. 207, No. 2, Feb. 15, 1995, pp. 621–629.

(Continued)

*Primary Examiner*—James Housel
*Assistant Examiner*—Zachariah Lucas
(74) *Attorney, Agent, or Firm*—Nikolai & Mersereau PA; C. G. Mersereau (57) ABSTRACT

The invention relates to methods and materials for use in the typing, diagnosis, prevention and/or treatment of prion disease.

17 Claims, 4 Drawing Sheets

OTHER PUBLICATIONS

"Copper Binding to the N–Terminal Tandem Repeat Region of Mammalian and Avian Prion Protein: Structural Studies Using Synthetic Peptides" by M.P. Hornshaw, et al, *Biochemical and Biophysical Research Communications*, vol. 214, No. 3, Sep. 25, 1995, pp. 993–999.

"Copper, iron and zinc in Alzheimer's disease senile plaques" by M.A. Lovell, et al, *Journal of the Neurological Sciences 158*, (1998), pp. 47–52.

"Reversibility of Scrapie Inactivation Is Enhanced by Copper" by Debbie McKenzie, et al, *The Journal of Biological Chemistry*, vol. 273, No. 40, Oct. 2, 1998, pp. 25545–25547.

"Metal–dependent α–helix formation promoted by the glycine–rich octapeptide region of prion protein" by Takashi Miura, et al, *Federation of European Biochemical Societies Letters 396*, (1996), pp. 248–252.

"Conversion of α–helices into β–sheets features in the formation of the scrapie prion proteins" by Keh–Ming Pan, et al, *Biochemistry*, vol. 90, Dec. 1993, pp. 10962–10966.

"Homozygous prion protein genotype predisposes to sporadic Creutzfeldt–Jakob disease" by Mark S. Palmer, et al, *Nature (Letters to Nature)*, vol. 352, Jul. 25, 1991.

"Molecular Basis of Phenotype Variability in Sporadic Creutzfeldt Jakob Disease" by Piero Parchi, MD, et al, *Annals of Neurology*, vol. 39, No. 6, Jun. 1996, pp. 767–778.

"Typing prion isoforms" by Gradimir N. Misevic, *Nature*, vol. 286, Mar. 20, 1997, pp. 232–233.

"Histopathological Similarities between Scrapie and Cuprizone Toxicity in Mice" by I.H. Pattison, et al, *Nature*, vol. 230, Mar. 12, 1971, pp. 115–117.

"Copper Stimulates Endocytosis of the Prion Protein" by Peter C. Pauly, et al, *The Journal of Biological Chemistry*, vol. 273, No. 50, Dec. 11, 1998, pp. 33107–33110.

"Molecular Biology of Prion Diseases" by Stanley B. Prusiner, *Science*, vol. 252, Jun. 14, 1998, pp. 1515–1521.

NMR structure of the mouse prion protein domain PrP (121–231) by Roland Riek, et al, *Nature (Letter to Nature)*, vol. 382, Jul. 11, 1996, pp. 180–182.

"Prion Protein Selectively Binds Copper (II) Ions" by Johannes Stöckel, et al, *Biochemistry*, 1998, vol. 37, No. 20, pp. 7185–7193.

"Evidence for the Conformation of the Pathologic Isoform of the Prion Protein Enciphering and Propagating Prion Diversity" by Glenn C. Telling, et al, *Science*, vol. 274, Dec. 20, 1996, pp. 2079–2082.

"Copper binding to the prion protein: Structural implications of four identical copperative binding sites" by John H. Viles, et al, *Biophysics*, vol. 96, Mar. 1999, pp. 2042–2047.

"Strain–specific prion–protein conformation determined by metal ions" by Jonathan D.F. Wadsworth et al, *Nature Cell Biology*, vol. 1, May 1999, pp. 55–59.

"A new variant of Creutzfeldt–Jakob disease in the UK" by R.G. Will, et al, *The Lancet*, vol. 347, Apr. 6, 1996, pp. 921–925.

* cited by examiner

METHOD TO TYPE PRION PROTEINS

The present application is a continuation of co-pending PCT International Application No. PCT/GB00/01327, having an International filing date of Apr. 7, 2000 and a priority date of Apr. 9, 1999 and entitled "METHOD TO TYPE PRION PROTEINS".

The present invention relates to the provision of materials and methods for the diagnosis, prevention and/or treatment of disease. In particular, spongiform encephalopathies or any disease associated with prion proteins.

Prions are infectious pathogens that differ from bacteria, fungi, parasites, viroids, and viruses, both with respect to their structure and with respect to the diseases that they cause. Molecular biological and structural studies of prions promise to open new vistas into fundamental mechanisms of cellular regulation and homeostasis not previously appreciated. Kuru, Creutzfeldt-Jakob disease (CJD), fatal familial insomnia (FFI) and Gerstmann-Sträussler-Scheinker syndrome (GSS) are all human neurodegenerative diseases that are caused by prions and are frequently transmissible to laboratory animals. Familial CJD and GSS are also genetic disorders. No effective therapy exists to prevent these fatal disorders.

In addition to the prion diseases of humans, disorders of animals are included in the group of known prion diseases. Scrapie of sheep and goats is the most studied of the prion diseases. Bovine spongiform encephalopathy (BSE) is thought to result from abnormal feeding practices. BSE threatens the beef industry of Great Britain and possibly other countries; the production of pharmaceuticals involving cattle is also of concern. Control of sheep scrapie in many countries is a persistent and vexing problem.

Prion diseases are associated with the accumulation of a conformational isomer ($PrP^{Sc}$) of host-derived prion protein ($PrP^c$) with an increase in its β-sheet content. According to the protein-only hypothesis, $PrP^{Sc}$ is the principal or sole component of transmissble prions. Although the structure of $PrP^c$ has been determined and has been found to consist predominantly of α-helices, the insolubility of $PrP^{Sc}$, which is isolated from tissue in a highly aggregated state and which has a high β-sheet content, has precluded high-resolution structural analysis.

The detection of the disease-associated isoform of prion protein, $PrP^{Sc}$, in brain or other tissues from patients is thought to be diagnostic of prion disease.

Figure 1:
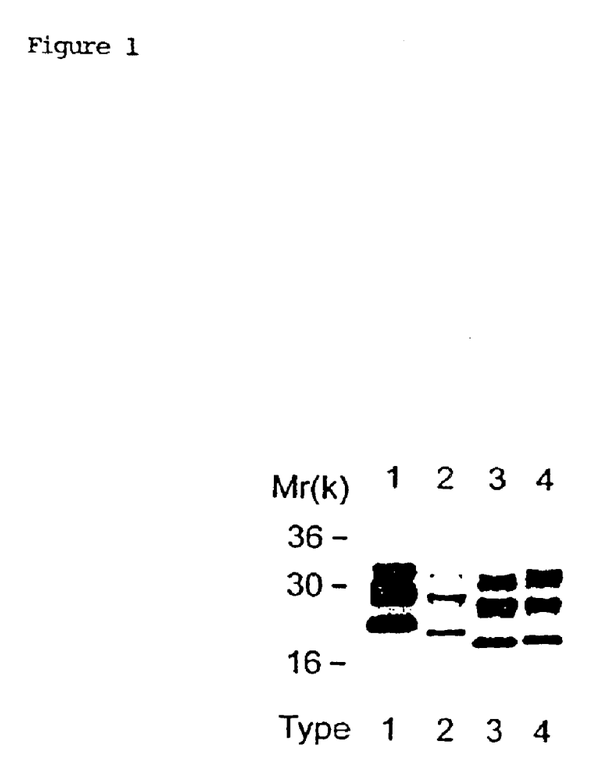

Previously, we have identified four human $PrP^{Sc}$ types or strains that are is associated with distinct forms of sporadic or acquired Creutzfeldt-Jakob disease (CJD)[2]. Type 4 $PrP^{Sc}$ characterises new variant CJD (vCJD), causally related to bovine spongiform encephalopathy[14] while there is no evidence for an animal origin for the prion strains causing classical CJD ($PrP^{Sc}$ types 1–3)[12]. Following limited proteolysis with proteinase K (PK) and Western blotting these distinct types of $PrP^{Sc}$ can be readily distinguished by differing fragment sizes or relative differences in intensities of the three PrP glycoforms (corresponding to amino-terminally truncated cleavage products generated from di-, mono-, or non-glycosylated $PrP^{Sc}$)[2] (FIG. 1). A common PrP polymorphism (with either methionine (M) or valine (V) at residue 129) contributes to genetic susceptibility to both sporadic and acquired human prion disease[13,14]. To date, types 1 and 4 $PrP^{Sc}$ have been found only in individuals of the MM genotype, type 2 is seen with all genotypes (MM, MV and VV) and type 3 $PrP^{Sc}$ only with genotypes MV or VV ([2,15,16] and unpublished data).

Figure 2:
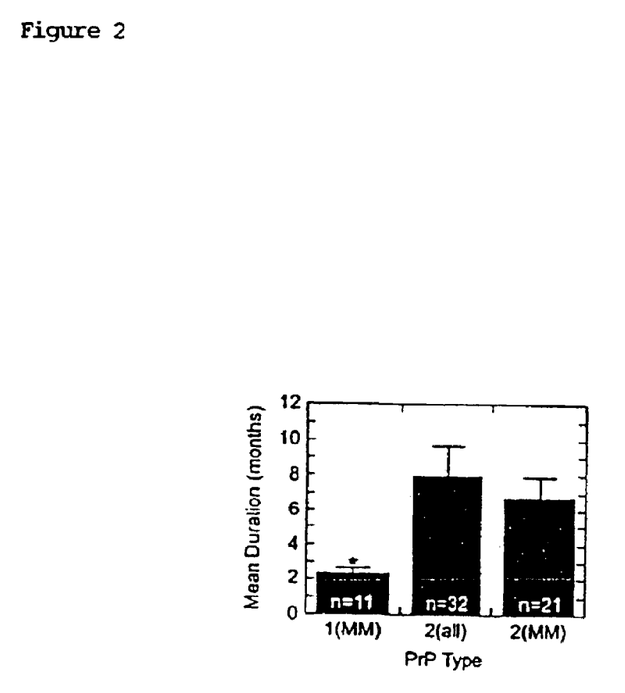

An earlier study[17] of $PrP^{Sc}$ types in classical CJD had described only two types of $PrP^{Sc}$ and these authors have argued that the types 1 and 2 we describe correspond to their type 1, while our type 3 pattern corresponds to their type 2[18]. However, these authors concede a degree of heterogeneity in their type 1 cases[17]. We have performed a large-scale study of $PrP^{Sc}$ types in CJD in conjunction with the UK National CJD Surveillance Unit. Comprehensive phenotypic assessment of patients and $PrP^{Sc}$ typing were performed blind. A detailed study will be published elsewhere, but we have been able to demonstrate that patients classified as type 1 and type 2 using our criteria have quite distinct phenotypes (FIG. 2), confirming the validity of our molecular classification. Type 1 human CJD is a distinct human prion disease with an aggressive clinical course and remarkably short clinical duration. These observations are consistent with $PrP^{Sc}$ conformation being the foundation of prion strain diversity.

According to the invention there is provided methods suitable for typing $PrP^{Sc}$ and methods of altering the conformation of $PrP^{Sc}$. Also provided is the use of agents capable of affecting the binding of $PrP^{Sc}$ to one or more divalent metal ions and methods of screening for and using agents capable of converting type 1 $PrP^{Sc}$ to type 2 $PrP^{Sc}$ or type 2⁻ $PrP^{Sc}$ and vice versa and/or type 2 $PrP^{Sc}$ to type $2^-$ $PrP^{Sc}$ and vice versa. These aspects of the invention are defined in the accompanying claims and/or described hereinafter.

The disease-related isoform of PrP, $PrP^{Sc}$, is distinguished biochemically from the normal cellular isoform of the protein, $PrP^{c}$, by its partial resistance to digestion with the enzyme proteinase K(PK). PK will completely digest $PrP^{c}$ but only removes a protease-sensitive N terminal portion of $PrP^{Sc}$, under the conditions specified in the methods section.

By "affecting the binding of $PrP^{Sc}$ one or more divalent metal ions" we include the meaning that the occupancy of the metal binding sites is altered. Preferably this alteration gives rise to a change in the conformation of $PrP^{Sc}$ and changes in conformation can be observed by subjecting the $PrP^{Sc}$ to digestion and electrophoresis as described herein. This form of $PrP^{Sc}$ is referred to herein as type $2^-$ $PrP^{Sc}$ and constitutes a further aspect of the invention.

More preferably, the change in conformation results in a form of $PrP^{Sc}$ which exhibits a lower apparent molecular mass than type 1 and/or type 2 $PrP^{Sc}$ when subjected to digestion and electrophoresis as described herein.

The ability of an agent to convert type 1 $PrP^{Sc}$ to type 2 $PrP^{Sc}$ can be determined by exposing type 1 $PrP^{Sc}$ type to the agent then subjecting the $PrP^{Sc}$ to digestion and electrophoresis as described herein and comparing the digestion products with type 2 $PrP^{Sc}$ digestion products under the same conditions. If the products are the same, conversion to type 2 is indicated.

The prion disease may be selected from one or more of the diseases affecting humans. Alternatively or additionally, the prion diseases are selected from one or more of the diseases which affect domestic farm animals such as cows, sheep and goats. Other prion diseases include transmissible mink encephalopathy; chronic wasting disease of mule deer and elk, bovine spongiform encephalopathy and, more recently, a whole series of new animal diseases that are thought to have arisen from their dietary exposure to the BSE agent. These include feline spongiform encephalopathy, affecting domestic cats and captive wild cats (such as cheetahs, pumas, ocelots, tigers) and spongiform encephalopathies of captive exotic ungulates (including kudu, nyala, gemsbok, eland).

Whilst the invention has been described using human $PrP^{Sc}$ as an illustrative example, skilled persons will appreciate that the invention is intended to embrace $PrP^{Sc}$ from any animal which is susceptible to a prion disease including the animals mentioned above, but especially bovine or ovine $PrP^{Sc}$.

The ability of the agents of the invention to alter the conformation of $PrP^{Sc}$ may be especially important for inherited prion disease. That is, early diagnosis of inherited mutation through prion gene analysis eg from blood samples, may allow therapeutic intervention, for example administration of agents which do not favour the type 1 $PrP^{Sc}$ conformation eg divalent metal ion chelators, especially $Cu^{2+}$ and/or $Zn^{1+}$ chelators, if genetic predisposition to type 1 and/or type 2 $PrP^{Sc}$ propagation is indicated.

Methods of detecting genetic predisposition to type 1 and/or type 2 $PrP^{Sc}$ propagation are described in an International (PCI) application No. PCT/GB97/02843, published as WO98/16834 and incorporated herein by reference.

Copper chelating therapies currently used in the treatment of Wilson's disease may be useful in the prevention and/or treatment of prion disease. The chelators penicillamine (proprietary names Cuprimine, Cupren, Depen, Distamine, D-penamine, Gerondyl, Kelatin, Metalcaptase, Pendramie, Sufortan, Sufortanan, and Trolvol); Trientine dihydrochloride (proprietary name Syprine) and Dimercaprol (Proprietory name Sulfactin Homburg) are all drugs currently licenced for human use. Divalent metal ion supplements, especially copper supplements and zinc supplements may also be useful in the treatment and/or prevention of prion disease. There are many copper and zinc supplements that are available for human use.

The invention also provides a kit comprising means for carrying out the methods of the invention.

The invention also provides a kit useful for diagnosing a prion disease comprising as described herein.

Preferably, in the methods of the invention the sample comprises or consists of a bodily tissue or fluid, which may be blood or a derivative of blood, ie a component such as plasma, or is derived from lymphoid tissue (such as tonsils, appendices, lymph nodes, spleen) or brain or is cerebrospinal fluid, or faeces, urine or sputum, for example. The biological sample may be a tissue sample eg a biopsy tissue sample.

Preferred non-limiting methods and examples which embody certain aspects of the invention will now be described in which:—

FIG. 1.

Western blot of human $PrP^{Sc}$ types 14 following protease K treatment using anti-PrP monoclonal 3F4. Lane 1, type 1 $PrP^{Sc}$, PRNP 129MM; lane 2, type 2 $PrP^{Sc}$, PREP 129MM; lane 3, type 3 $PrP^{Sc}$, PRNP 129VV; lane 4, type 4 $PrP^{Sc}$, PRNP 129MM.

FIG. 2.

Mean duration of illness for CJD patients with $PrP^{Sc}$ types 1 and 2. Duration in type 1 cases is significantly different from type 2 regardless of PRNP codon 129 genotype ($p<0.004$; Mann-Whitney U test).

FIG. 3.

Proteinase K digestion of human $PrP^{Sc}$ in the presence of metal chelators.

(a, b) Effects of EDTA on digestion of $PrP^{Sc}$ types 1–4.10% w/v brain homogenates prepared in cold lysis buffer were proteinase K treated directly (denoted −) or after (denoted +) adjustment of EDTA to 20 mM final concentration. (a) Lane 1 and 2, type 1 $PrP^{Sc}$; lane 3 and 4, type 2 $PrP^{Sc}$, 129M. (b) Lane 1 and 2, type 1 $PrP^{Sc}$ 129 genotype MM; lane 3 and 4, type 2 $PrP^{Sc}$, 129 genotype MM; lane 5 and 6, type 3 $PrP^{Sc}$, 129 genotype MV; lane 7 and 8, type 4 $PrP^{Sc}$, 129 genotype MM.

(c) The effect of EDTA on type 1 $PrP^{Sc}$ is consistent in different buffers. 10% w/v brain homogenates from a type 1 $PrP^{Sc}$ patient were prepared in cold lysis buffer (CLB) (lanes 1 and 2), PBS (lanes 3 and 4) or N-ethylmorpholine buffer (M) (lanes 5 and 6) and proteinase K digested before (denoted −) or after (denoted +) adjustment with EDTA to 20 mM final concentration.

(d) EDTA exposes a new proteinase K cleavage site on type 1 $PrP^{Sc}$. Aliquots of a 10% w/v PBS brain homogenate from a type 1 $PrP^{Sc}$ patient were western blotted directly (no proteinase K treatment) in the absence (lane 1) or presence (lane 2) of 25 mM EDTA. In lanes 3–5, aliquots of a 10% w/v PBS brain homogenate from a type 1 $PrP^{Sc}$ patient were proteinase K treated in the absence (lanes 3 and 5) or presence (lane 4) of 25 mM EDTA. Following proteolysis, the sample in lane 5 was boiled in SDS sample buffer and subsequently adjusted to 25 mM EDTA prior to electrophoresis.

(e, f) Effects of different chelators on the digestion of type 1 $PrP^{Sc}$. Aliquots of a 10% w/v N-ethylmorpholine buffer brain homogenate from a type 1 $PrP^{Sc}$ patient were proteinase K treated in the absence (lanes 1) or presence (lanes 2–7) of different chelators. The chelators and their final concentrations were: (e) lane 2, 20 mM EDTA; lane 3, 20 mM EGTA; lane 4, 20 mM dipicolinic acid; lane 5, 20 mM bathophenanthroline disulfonic acid; lane 6, 20 mM neocuproine; lane 7, 20 mM 1, 10 phenanthroline. (f) lane 2, 20 mM EDTA; lane 3, 20 mM EGTA; lane 4, 20 mM triethylenetetramine; lane 5, 20 mM dipicolinic acid; lane 6, 10 mM triethylenetetramine plus 10 mM dipicolinic acid; lane 7, 10 mM triethylenetetramine plus 10 mM bathophenanthroline disulfonic acid.

FIG. 4.

Washing $PrP^{Sc}$ type 1 and type 2 (PRNP 129MM) in the presence of various metal ions.

(a) Type 1 $PrP^{Sc}$. Aliquots of a 10% w/v brain homogenate from a type 1 $PrP^{Sc}$ patient prepared in PBS were proteinase K digested before (lane 1) or after washing with either N-ethylmorpholine buffer alone (lane 2) or the same buffer containing, 20 $\mu$M $FeCl_3$, 1 mM $MgCl_2$, 1 $\mu$M $NiCl_2$, 2 mM $CaCl_2$, 0.05 $\mu$M $MnCl_2$, and 0.03 $\mu$M $CoCl_2$ (lane 3); 110 $\mu$M $ZnCl_2$ (lane 4); 20 $\mu$M $ZnCl_2$ (lane 5); 10 $\mu$M $CuSO_4$ (lane 6); 20 $\mu$M $CuSO_4$ (lane 7); 25 $\mu$M $CuSO_4$ (lane 8).

(b) Type 1 $PrP^{Sc}$. Aliquots of a 10% w/v brain homogenate from a type 1 $PrP^{Sc}$ patient prepared in PBS were proteinase K digested before (lane 1) or after washing with N-ethylmorpholine buffer (lanes 24). Following proteolysis and prior to electrophoresis, samples in lanes 3 and 4 were washed with N-ethylmorpholine buffer containing either 20 $\mu$M $ZnCl_2$, (lane 3) or 25 $\mu$M $CuSO_4$, (lane 4).

(c) Type 1 $PrP^{Sc}$. Aliquots of a 10% w/v brain homogenate from a type 1 $PrP^{Sc}$ patient prepared in N-ethylmorpholine buffer were proteinase K digested after washing with either N-ethylmorpholine buffer alone (lane 1) or the same buffer containing, 20 $\mu$M $ZnCl_2$ (lane 2); 30M $NiCl_2$ (lane 3); 30 $\mu$M $CoCl_2$ (lane 4); 30 $\mu$M $MnCl_2$ (lane 5); or 30 $\mu$M $FeCl_3$ (lane 6).

(d) Type 2 $PrP^{Sc}$. Aliquots of a 10% w/v brain homogenate from a type 2 $PrP^{Sc}$ patient prepared in cold lysis buffer were proteinase K digested before (lane 1) or after washing with either N-ethylmorpholine buffer alone (lane 2) or the same buffer containing, 20 $\mu$M $ZnCl_2$, (lane 3) or 25 $\mu$M $CuSO_4$, (lane 4). Lanes 5 and 7 show digestion products from a type 1 $PrP^{Sc}$ PBS homogenate which was proteinase K treated directly (lane 5) or after addition of 25 mM EDTA (lane 6).

METHODS

1. Western Blot Analysis

All procedures were carried out in a microbiological containment level 3 facility with strict adherence to safety protocols. 10% w/v brain homogenates from human brain tissue obtained at autopsy from patients with CJD were prepared in the following solutions: cold lysis buffer (10 mM Tris, 100 mM EDTA pH 7.4 containing 100 mM NaCl, 0.5% w/v NP-40 and 0.5% w/v sodium deoxycholate); phosphate buffered saline (PBS) (Dulbecco's sterile PBS lacking $Ca^{2+}$ and $Mg^+$; Sigma); N-ethylmorpholine buffer (25 mM N-ethylmorpholine pH 7.4 containing 0.5% w/v NP-40). Samples were adjusted to a final concentration of 50 μg/ml proteinase K (Merck) and incubated at 37° C. for 1 h. Digestion was terminated by addition of an equal volume of 2×SDS sample buffer (125 mM Tris-HCl, 20% v/v glycerol pH 6.8 containing 4% w/v SDS, 4% v/v 2-mercaptoethanol, 8 mM 4-(2-aminoethyl)-benzene sulfonyl fluoride and 0.02% w/v bromophenol blue) and immediate transfer to a 99° C. heating block for 10 min. Samples were analysed by electrophoresis and western blotting using anti-PrP monoclonal antibody 3F4 as described previously.

2. Chelation Studies

Chelators were added to brain homogenates as aliquots from stock solutions. EDTA was prepared as either a 100 or 250 mM stock in water and titrated to pH 8.0 with NaOH. Other chelators (see legend to FIG. 3) were prepared similarly as 100 mM stock solutions pH 8.0, with the exception of 1, 10 phenanthroline and neocuproine which were prepared as 100 mM stocks in 50% v/v ethanol in water. All chelators were obtained from Sigma. Physical properties of the various chelators used and the stability constants of complexes formed with various metal ions are detailed elsewhere[33].

3. Metal Supplementation Studies

10 μl aliquots of 10% w/v brain homogenates were centrifuged for 10 min. at 14,000 rpm in a microfuge after which supernatants were removed and discarded. Pellets were thoroughly resuspended in 500 μl 25 mM N-ethylmorpholine pH 7.4 containing 0.5% w/v NP-40 which either lacked or contained various metal salts as detailed in the legend to FIG. 4. Following incubation for ⁻10 min at room temperature, samples were centrifuged (15 min at 14,000 rpm in a microfuge) after which the supernatant was discarded. Each aspirated pellet was resuspended appropriately with the analogous solution to a final volume of 101 and treated with proteinase K. In some experiments samples were washed with metal solutions after proteinase K digestion.

EXAMPLES AND RESULTS

1. Types 1 and 2 $PrP^{Sc}$ Conformations Depend on Metal Ions

Figure 3:
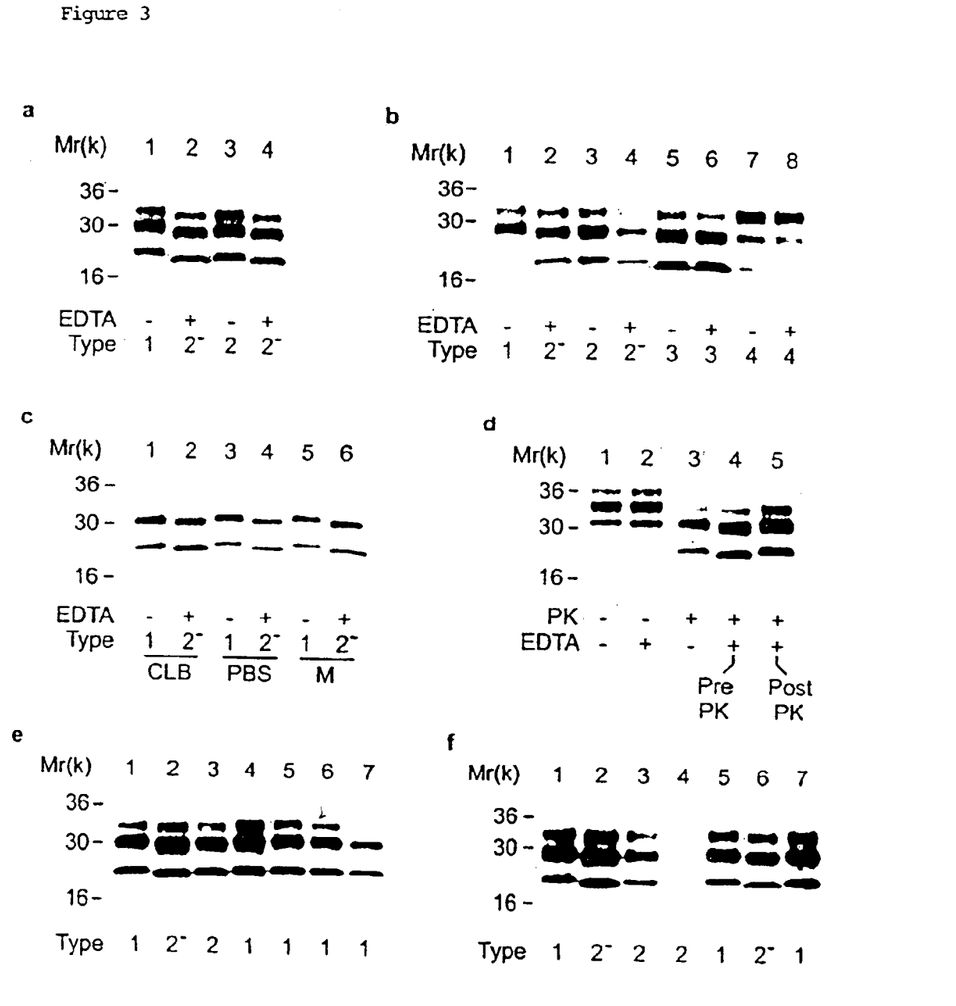

In an attempt to elucidate the molecular basis of this strain variation, we have investigated the biochemical properties of type 1 and 2 human $PrP^{Sc}$. All patients studied were of PRNP codon 129 genotype MM. When type 1 and type 2 $PrP^{Sc}$ were treated with 20 mM EDTA, prior to treatment with PK, the pattern of cleavage was changed. Rather than producing their distinct patterns, both types gave indistinguishable and common fragment sizes (FIG. 3a). As these digestion products migrate with lower molecular mass than either type 1 or type 2, we designated this type 2⁻. In marked contrast, treatment with EDTA did not alter the generation of characteristic cleavage products from $PrP^{Sc}$ types 3 or 4 (FIG. 3b).

The generation of type 2⁻ cleavage products from type 1 $PrP^{Sc}$ typically required final EDTA concentrations in the range of 15–20 mM, no further change was elicited by higher chelator concentrations (data not shown). This action of EDTA was fully reproducible (>60 repetitions using samples from nine separate type 1 patients) and occurred irrespective of the buffer in which brain homogenates were prepared (FIG. 3c). Nine homogenates from type 1 and type 2 patients were analysed before and after EDTA treatment. In each case the expected shift of type 1 or type 2 to type 2⁻ was detected. We have estimated the shift in apparent molecular mass from type 1 to type 2 and type 2 M129 to type 2⁻ to be 1.1±0.3 kDa (mean±SD; n=9) and 0.65±0.3 kDa (mean±SD; n=9), respectively. There was no significant alteration in the ratios of the three principal PrP glycoforms.

Importantly, the possibility that EDTA itself directly influenced electrophoretic mobility was excluded. Without protease digestion, type 1 $PrP^{Sc}$ samples migrated equivalently in the presence or absence of EDTA FIG. 3d). Similarly, application of EDTA to type 1 $PrP^{Sc}$ samples after proteolysis had no effect (FIG. 3d). Collectively, these findings suggest that the respective conformations of type 1 $PrP^{Sc}$ and type 2 $PrP^{Sc}$ M129 depend upon the presence of metal ions and that metal chelation induces a conformational change which exposes a new proteolytic cleavage site that is apparently common to both metal-depleted conformers.

2. Effects of Metal-Selective Chelators

As the amino-terminal octapeptide repeat region of PrP has been shown to bind $Cu^{2+}$[-24], we considered a role for $Cu^{2+}$ in determining metal-dependent $PrP^{Sc}$ conformation. However, the use of various metal-selective chelating agents revealed a more complex situation. In contrast to the effects of EDTA (a broad specificity chelator with high affinity for many divalent metal ions), other more selective chelators, including those with high affinity for $Cu^{2+}$ (EGTA; triethylenetetramine), $Cu^{2+}$ (neocuproine), $Zn^{2+}$ (dipicolinic acid; 1, 10 phenanthroline) or $Fe^{2+}$ (1, 10 phenanthroline; bathophenanthroline disulfonic acid) were unable to precisely mirror this action (FIGS. 3e and f). However, the effectiveness of combined application of triethylenetetrarine and dipicolinic acid (FIG. 3f) suggested that chelation of both $Cu^{2+}$ and $Zn^{2+}$ may be required for generation of type 2 cleavage products from type 1 $PrP^{Sc}$.

3. Both $Cu^+$ and $Zn^{2+}$ Interact with $PrP^{Sc}$

Figure 4:
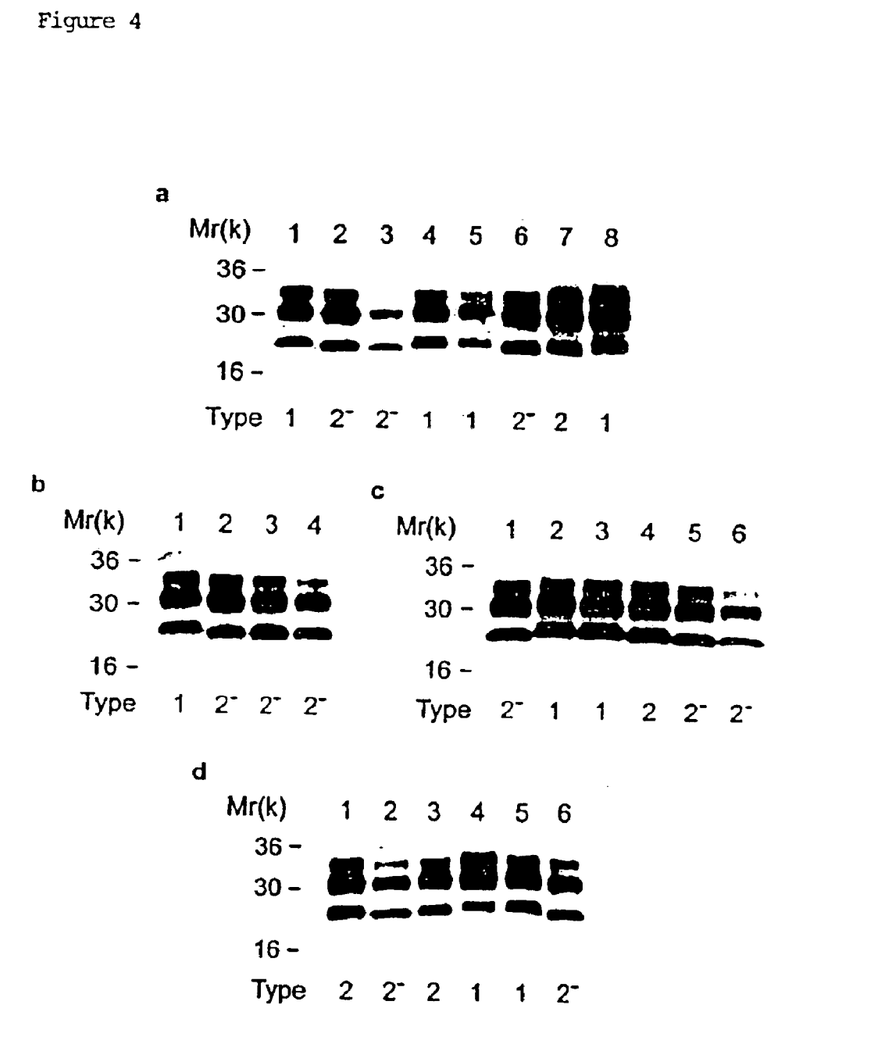

To study this further we developed an alternative method for probing the metal dependency of $PrP^{Sc}$ conformation by washing the homogenates to strip bound metal from the protein. We found that washing type 1 $PrP^{Sc}$ homogenates with N-ethylmorpholine buffer (equivalent to 0.5000 fold dilution) prior to protease digestion readily resulted in the formation of type 2⁻ digestion products (FIGS. 4a and b). Repetition of this procedure using buffers supplemented with various metal ions at total concentrations observed in serum[25] convincingly demonstrated that the type 1 conformation is dependent on metal ions. In the maintained presence of $Cu^{2+}$ or $Zn^{2+}$, digestion products closely resembled those generated from untreated type 1 $PrP^{Sc}$ (FIG. 4a), that is the original $PrP^{Sc}$ conformation was retained. Other metal ions when present at their respective total concentration found in serum had no effect, either when applied separately (not shown) or together (FIG. 4a). Importantly, anomalous electrophoretic mobility of cleavage products in the presence of $Cu^{2+}$ or $Zn^{2+}$ can be excluded. Exposure of metal-depleted and proteinase K digested type 1 $PrP^{Sc}$ samples to either $Cu^{2+}$ or $Zn^{2+}$ prior to and during electrophoresis had no effect (FIG. 4b). Collectively, these findings (coupled with results obtained using metal-selective chelators) implicate $Cu^{2+}$ or $Zn^{2+}$ as the most relevant metal ions that interact with type 1 $PrP^{Sc}$ in prion diseased brain. Notably, the concentrations of $Cu^{2+}$ which we find effective in maintaining type 1 PrP$^{Sc}$ conformation correlate closely with the 14 μM dissociation constant of Cu$^{2+}$ binding to recombinant full length hamster PrP[3]. Although in normal brain both Cu$^{2+}$ and Zn$^+$ are present at much higher total concentrations compared to serum (discussed in references[23,25]), these metals would predominantly exist in protein complexes rather than as free ions. While Zn$^{2+}$ can attain transient extracellular total concentrations as high as 300 μM in brain during sustained neuronal activity[26], the proportion that exists as free ions is uncertain. In the case of Cu$^{2+}$, micromolar levels of free ions in any cell compartment seems highly unlikely in the physiological state, and it thus remains to be demonstrated how PrP$^C$ might acquire Cu$^{2+}$ in vivo. From our findings however, the pathological relevance of metal ion binding to PrP$^{Sc}$ is clear, PrP$^{Sc}$ type 1 and 2 are isolated from diseased brain in metal occupied form. These findings could suggest that the concentrations of Cu$^{2+}$ and Zn$^{2+}$ in prion-diseased brain are grossly perturbed. This has recently been demonstrated to be the case in Alzheimer's disease, where copper, zinc and iron are highly concentrated within the periphery and core of senile plaque deposits[27]. Moreover, micromolar concentrations of Cu$^{2+}$ and Zn$^{2+}$ can induce dramatic aggregation of amyloid Aβ protein[25]. In the latter study, at total concentrations of metal ions found in serum, only Cu$^{2+}$ and Zn$^{2+}$ were able to induce aggregation of Aβ protein, however, at supra-physiological concentrations (30 μM) Ni$^{2+}$ and Co$^{2+}$ were also effective. We have also tested the effectiveness of 30 μM Ni$^{2+}$, Co$^{2+}$ and Mn$^{2+}$ in maintaining type 1 PrP$^{Sc}$ conformation, and find that at this concentration only Ni$^{2+}$ can effectively substitute for Cu$^{2+}$ or Zn$^{2+}$ FIG. 4c). These findings further reinforce our deduction that Cu$^{2+}$ and Zn$^{2+}$ are likely to be the most important metal ions that interact with PrP$^{Sc}$ in prion diseased brain.

4. Inter-Conversion of Types 1 and 2 Human PrP$^{Sc}$

Interestingly, whereas type 1 PrP$^{Sc}$ conformation could be readily maintained in the presence of 10 μM Zn$^{2+}$, higher concentrations of Cu$^{2+}$ were required to have the same effect. We examined a range of Cu$^{2+}$ concentrations (10–25 μM) and at 20 μM were able to observe a pattern of cleavage products which migrated with a mobility similar to that of the type 2 products, that is intermediate between type 1 and type 2$^-$ (compare FIG. 4a, lanes 6–8). This intermediate pattern can also be discerned after digestion of type 1 PrP$^{Sc}$ in the presence of the copper-selective chelators EGTA or triethylenetetramine (FIGS. 3e and f), or after washing and digestion of type 1 PrP$^{Sc}$ in the presence of 30 μM Co$^{2+}$ (FIG. 4c). As the mobility of these intermediate fragments closely resemble type 2 cleavage products, these findings suggest that the conformations of type 1 PrP$^{Sc}$ and type 2 PrP$^{Sc}$ differ principally with respect to the relative occupancy of their metal binding sites.

In order to study this further we examined the effects of applying exogenous metals to type 2 PrP$^{Sc}$. Consistent with findings for type 1 PrP$^{Sc}$, washing insoluble aggregates of type 2 PrP$^{Sc}$ with buffer alone gave type 2$^-$ cleavage products (FIG. 4d). However, in the maintained presence of different concentrations of Cu$^{2+}$ or Zn$^{2+}$, we observed either the original type 2 pattern of digestion products, or a new pattern of higher molecular mass cleavage fragments closely similar to those generated from untreated type 1 PrP$^{Sc}$ (FIG. 4d). These findings imply that the conformations of type 1 PrP$^{Sc}$ and type 2 PrP$^{Sc}$ are interchangeable and depend on the level of: occupancy with these metals.

Discussion

The demonstration that phenotypically distinct types of CJD are associated with the biochemically distinct types 1 and 2 PrP$^{Sc}$ clarifies earlier confusion on classification of CJD sub-types[18]. The precise aetiology of sporadic CJD remains obscure. The spontaneous conversion of PrP$^C$ to PrP$^{Sc}$ as a rare stochastic event, or somatic mutation of the PrP gene, resulting in expression of a pathogenic PrP mutant[12], are plausible explanations. However, other causes, including environmental exposure to human or animal prions is not ruled out by epidemiological studies[28] as a cause of at least some cases. "Sporadic" CJD may have multiple aetiologies. These findings immediately allow a more precise molecular classification of human prion disease, with important implications for epidemiological studies into the aetiology of sporadic CJD. Re-analysis of epidemiological data using these molecular sub-types may reveal important risk factors obscured when sporadic CJD is analysed as a single entity.

These findings also elucidate a potential molecular mechanism for strain variation. The ability of metal ions to directly influence PrP$^{Sc}$ conformation has widespread implications for understanding strain diversity in human and animal prion diseases. This demonstration of an interaction between PrP$^{Sc}$ and Cu$^{2+}$ not only supports recent work indicating that Cu$^{2+}$ may stabilise PrP$^{Sc}$ conformation[29], but provides further evidence suggesting that the neuropathology of prion diseases may be related to abnormalities in copper-metabolism[22,30-32]. The present work suggests that drugs which influence copper metabolism may have therapeutic potential in prion disease.

5. Exemplary Pharmaceutical Formulations of the Invention

The formulations may conveniently be presented in unit dosage form and may be prepared by any of the methods well known in the art of pharmacy.

Such methods include the step of bringing into association the active ingredient (ie agent which affects the binding of divalent metal ions to PrP$^{Sc}$) with the carrier which constitutes one or more accessory ingredients. In general the formulations are prepared by uniformly and intimately bringing into association the active ingredient with liquid carriers or finely divided solid carriers or both, and then, if necessary, shaping the product.

Whilst it is possible for an agent e.g., compound of the invention to be administered alone, it is preferable to present it as a pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen free.

Formulations in accordance with the present invention suitable for oral a ministration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient-in a suitable liquid carrier.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The following examples illustrate pharmaceutical formulations according to the invention in which the active ingredient is selected from one or more of antibodies and agents eg compounds of the invention:

Example A

Tablet

| Active ingredient | 100 mg |
|---|---|
| Lactose | 200 mg |
| Starch | 50 mg |
| Polyvinylpyrrolidone | 5 mg |
| Magnesium stearate | 4 mg |
| | 359 mg |

Tables are prepared from the foregoing ingredients by wet granulation followed by compression.

Example B

Opthalmic Solution

| Active ingredient | 0.5 g |
|---|---|
| Sodium chloride, analytical grade | 0.9 g |
| Thiomersal | 0.001 g |
| Purified water to | 100 ml |
| pH adjusted to | 7.5 |

Example C

Tablet Formulations

The following formulations A and B are prepared by wet granulation of the ingredients with a solution of povidone, followed by addition of magnesium stearate and compression.

| Formulation A | | |
|---|---|---|
| | mg/tablet | mg/tablet |
| (a) Active ingredient | 250 | 250 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 500 | 300 |

| Formulation B | | |
|---|---|---|
| | mg/tablet | mg/tablet |
| (a) Active ingredient | 250 | 250 |
| (b) Lactose | 150 | — |
| (c) Avicel PH 101 ™ | 60 | 26 |
| (d) Povidone B.P. | 15 | 9 |
| (e) Sodium Starch Glycolate | 20 | 12 |
| (f) Magnesium Stearate | 5 | 3 |
| | 500 | 300 |

| Formulation C | |
|---|---|
| | mg/tablet |
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose used in formulation E is of the direction compression type.

Formulation D

| | mg/capsule |
|---|---|
| Active Ingredient | 250 |
| Pregelatinised Starch NF15 | 150 |
| | 400 |

Formulation E

| | mg/capsule |
|---|---|
| Active Ingredient | 250 |
| Lactose | 150 |
| Avicel ™ | 100 |
| | 500 |

Formulation F (Controlled Release Formulation)

The formulation is prepared by wet granulation of the ingredients (below) with a solution of povidone followed by the addition of magnesium stearate and compression.

| | | mg/tablet |
|---|---|---|
| (a) | Active Ingredient | 500 |
| (b) | Hydroxypropylmethylcellulose (Methocel K4M Premium) ™ | 112 |
| (c) | Lactose B.P. | 53 |
| (d) | Povidone B.P.C. | 28 |
| (e) | Magnesium Stearate | 7 |
| | | 700 |

Drug release takes place over a period of about 68 hours and is generally complete after 12 hours.

Example D

Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

| | | mg/capsule |
|---|---|---|
| (a) | Active ingredient | 250 |
| (b) | Lactose B.P. | 143 |
| (c) | Sodium Starch Glycolate | 25 |
| (d) | Magnesium Stearate | 2 |
| | | 420 |

Formulation C

| | | mg/capsule |
|---|---|---|
| (a) | Active ingredient | 250 |
| (b) | Macrogol 4000 BP | 350 |
| | | 600 |

Capsules are prepared by melting the Macrogol 4000 BP, dispersing the active ingredient in the melt and filling the melt into a two part hard gelatin capsule.

Formulation D

| | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| | | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

Example E

Injectable Formulation

Active ingredient 0.200 g

Sterile, pyrogen free phosphate buffer (pH7.0) to 10 ml

The active ingredient is dissolved in most of the phosphate buffer (35–40° C.), then made up to volume and filtered through a sterile micropore filter into a sterile 10 ml amber glass vial (type 1) and sealed with sterile closures and overseals.

Example F

Intramuscular injection

| | |
|---|---|
| Active ingredient | 0.20 g |
| Benzyl Alcohol | 0.10 g |

-continued

| | |
|---|---|
| Glucofurol 75 ™ | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G

Syrup Suspension

| | |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H

Suppository

| | mg/suppository |
|---|---|
| Active ingredient (63 μm)* | 250 |
| Hard Fat, BP (Witepsol H15 - Dynamit Nobel) | 1770 |
| | 2020 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

6. Use in Medicine

The aforementioned pharmaceutical formulations and other formulations of the invention of agents which are capable of affecting the binding of divalent metal ions to $PrP^{Sc}$ may be administered in a variety of ways, for non-limiting example, by any conventional method including oral and parenteral (eg subcutaneous or intramuscular) injection. The treatment may consist of a single dose or a plurality of doses over a period of time, depending on the characteristics of the patient and/or the particular prion disease against which the treatment is directed.

The ability of the agents of the invention to alter the conformation of $PrP^{Sc}$ may be especially important for inherited prion disease. That is, early diagnosis of inherited mutation through prion gene analysis from blood samples may allow therapeutic intervention, for example administration of agents which do not favour the type 1 $PrP^{Sc}$ on conformation eg divalent metal ion chelators, especially $Cu^{2+}$ and/or $Zn^{2+}$ chelators, if genetic predisposition to type 1 and/or type 2 $PrP^{Sc}$ propagation is indicated.

7. Test Kit

Preferred components of a test kit may include:—

(i) Buffer solution of 25 mM N-ethylmorpholine buffer pH 7.4 containing 0.5% w/v NP-40

(ii) Stock solution of 250 mM EDTA prepared in water and titrated to pH 8.0 with NaOH (iii) 1 mg/ml stock proteinase K prepared in water (iv) 2×SDS sample buffer (125 mM Tris-HCl, 20% v/v glycerol pH 6.8 containing 4% w/v SDS, 4% v/v 2-mercaptoethanol, 8 mM 4-(2-aminoethyl)benzene sulfonyl fluoride and 0.02% w/v bromephenol blue)

8. Use of Test Kit

Prion diseased brain tissue is prepared as a 10% w/v homogenate in 25 mM N-ethylmorpholine buffer pH 7.4 containing 0.5% w/v NP-40. Aliquots of the samples are treated with proteinase K (50 μg/ml final for 1 h at 37° C.) either before or after adjustment with 250 mM EDTA pH 8.0 stock solution to give 20 mM final concentration of EDTA in the sample. Following digestion with proteinase K, samples are diluted with an equal volume of 2×SDS sample buffer and heated at 99° C. for 10 min. Samples are the subjected to SDS polyacrylamide gel electrophoresis. A change in the relative molecular mass of digestion products after treatment with EDTA is indicative of type 1 or type 2 $PrP^{Sc}$.

REFERENCES

1. Will, R. G. et al. A new variant of Creutzfeldt-Jakob disease in the UK. *Lancet* 347, 921–925 (1996).

2. Collinge, J., Sidle, K. C. L., Meads, J., Ironside, J. & Hill, A. F. Molecular analysis of prion strain variation and the aetiology of 'new variant' CJD. *Nature* 383, 680–690 (1996).

3. Bruce, M. E. et al. Transmissions to mice indicate that 'new variant' CJD is caused by the BSE agent. *Nature* 389, 498501 (1997).
4. Hill, A. F. et al. The same prion strain causes vCJD and BSE. *Nature* 389, 448450 (1997).
5. Prusiner, S. B. Molecular Biology of Prion Diseases. *Science* 252, 1515–1522 (1991).
6. Pan, K.-M. et al. Conversion of α-helices into β-sheets features in the formation of the scrapie prion proteins. *Proc. Natl. Acad. Sci. USA* 90, 10962–10966 (1993).
7. Rick, R. et al. NMR structure of the mouse prion protein domain PrP (121–231). *Nature* 382, 180182 (1996).
8. Bessen, R. A. & Marsh, R. F. Distinct PrP properties suggest the molecular basis of strain variation in transmissible mink encephalopathy. *J. Virol.* 68, 7859–7868 (1994).
9. Bessen, R. A. et al. Non-genetic propagation of strain-specific properties of scrapie prion protein. *Nature* 375, 698–700 (1995).
10. Telling, G. C. et al. Evidence for the conformation of the pathologic isoform of the prion protein enciphering and propagating prion diversity. *Science* 274, 2079–2082 (1996).
11. Caughey, B., Raymond, G. J. & Bessen, R. A. Strain-dependent differences in β-sheet conformations of abnormal prion protein. *J. Biol. Chem.* 273, 32230–32235 (1998).
12. Collinge, J. Human prion diseases and bovine spongiform encephalopathy (BSE). *Hum. Mol. Genet.* 6, 1699–1705 (1997).
13. Collinge, J., Palmer, M. S. & Dryden, A. J. Genetic Predisposition to Iatrogenic Creutzfeldt-Jakob disease. *Lancet* 337, 1441–1442 (1991).
14. Palmer, M. S., Dryden, A. J., Hughes, J. T. & Collinge, J. Homozygous prion protein genotype predisposes to sporadic Creutzfeldt-Jakob disease. *Nature* 352, 340–342 (1991).
15. Collinge, J., Beck, J., Campbell, T., Estibeiro, K. & Will, R. G. Prion protein gene analysis in new variant cases of Creutzfeldt-Jakob disease. *Lancet* 348, 56 (1996).
16. Hill, A. F. et al. Investigation of variant Creutzfeldt-Jakob disease and other human prion diseases with tonsil biopsy samples. *Lancet* 353, 183–189 (1999).
17. Parchi, P. et al. Molecular basis of Phenotypic Variability in Sporadic Creutzfeldt-Jakob Disease. *Ann. Neurol.* 39, 767–778 (1996).
18. Parchi, P. et al. Typing prion isoforms. *Nature* 386, 232–233 (1997).
19. Hornshaw, M. P., McDermott, J. R. & Candy, J. M. Copper binding to the N-terminal tandem repeat regions of mammalian and avian prion protein. *Biochem. Biophys. Res. Commun.* 207, 621629 (1995).
20. Hornshaw, M. P., McDermott, J. R., Candy, J. M. & Lakey, J. H. Copper binding to the N-terminal tandem repeat region of mammalian and avian prion protein: Structural studies using synthetic peptides. Biochem. *Biophys. Res. Commun.* 214, 993–999 (1995).
21. Miura, T., Hori-i, A. & Takeuchi, H. Metal-dependent α-helix formation promoted by the glycine-rich octapeptide region of prion protein. *FEBS Lett.* 396, 248–252 (1996).
22. Brown, D. R. et al The cellular prion protein binds copper in vivo. *Nature* 390, 684–687 (1997).
23. Stockel, J., Safar, J., Wallace, A. C., Cohen, F. E. & Prusiner, S. B. Prion protein selectively binds copper(II) ions. *Biochemistry* 37, 7185–7193 (1998).
24. Viles, J. H. et al. Copper binding to the prion protein: Structural implications of four identical cooperative binding sites. *Proc. Natl. Acad. Sci. USA* 96, 2042–2047 (1999).
25. Atwood, C. S. et al. Dramatic aggregation of Alzheimer Aβ by Cu(II) is induced by conditions representing physiological acidosis. *J. Biol. Chem.* 273, 12817–12826 (1998).
26. Assaf, S. Y. & Chung, S.-H. Release of endogenous $Zn^{2+}$ from brain tissue during activity. *Nature* 308, 734736 (1984).
27. Lovell, M. A. et al. Copper, iron and zinc in Alzheimer's disease senile plaques. *J. Neurol. Sc* 158, 47–52 (1998).
28. Collins, S. et al. Surgical treatment and risk of sporadic Creutzfeldt-Jakob disease: a case-control study. *Lancet* 353, 693697 (1999).
29. McKenzie, D. et al. Reversibility of scrapie inactivation is enhanced by copper. *J. Biol. Chem.* 273, 25545–25547 (1998).
30. Carlton, W. W. Spongiform encephalopathy induced in rats and guinea pigs by cuprizone. *Exp. Mol. Pathol.* 10, 274287 (1969).
31. Pattison, I. H. & Jebbett, J. N. Histopathological similarities between scrapie and cuprizone toxicity in mice. *Nature* 230, 115–117 (1971).
32. Pauly, P. C. & Harris, D. A. Copper stimulates endocytosis of the prion protein. *J. Biol. Chem.* 273, 33107–33110 (1998).
33. Dawson, R. M. C., Elliott, D. C, Elliott, W. H. & Jones, K. M. Eds. Stability constants of metal complexes. In: *Data for biochemical research*, $3^{rd}$ edition, Clarendon Press, Oxford, 399–415 (1986).

What is claimed is:

1. A method for typing $Prp^{Sc}$ comprising the steps of:
   (i) providing a first and second sample containing a $Prp^{Sc}$ protein;
   (ii) treating the first sample to remove $Cu^{2+}$ and $Zn^{2+}$ from $Prp^{Sc}$ wherein treatment involves treating the sample with a metal chelator or combination of chelators capable of chelating both $Cu^{2+}$ and $Zn^{2+}$;
   (iii) subsequently digesting both the first and second samples with proteinase K; and
   (iv) comparing, using side-by-side electrophoresis, the products of the digestion of the first and second samples to determine whether or not the products are the same or different; a difference being indicative of the presence of type 1 or type 2 $Prp^{Sc}$, and no difference being indicative of type 3 or type 4 $Prp^{Sc}$.

2. A method as claimed in claim 1, wherein the metal chelator includes EDTA.

3. A method as claimed in claim 2, wherein the EDTA is present at a concentration of about 15–20 mM.

4. A method as claimed in claim 1, wherein step (ii) involves washing the $Prp^{Sc}$ sample with a buffer.

5. A method as claimed in claim 4, wherein the buffer is a morpholine buffer.

6. A method as claimed in claim 1, wherein the digestion products of a first sample comprising $Prp^{Sc}$ type 1 or type 2 migrate with a lower molecular mass than the digestion products of the second sample when subjected to electrophoresis under the same conditions.

7. A method as claimed in claim 6, wherein a reduction in apparent molecular mass of 1.1±0.3 kDa (mean±SD, n=9) is indicative of type 1 $Prp^{Sc}$.

8. A method as claimed in claim 6, wherein a reduction in apparent molecular mass of 0.65±0.3 kDa (mean±SD, n=9) is indicative of type 2 $Prp^{Sc}$.

9. A method as claimed in claim 1 wherein the sample comprises any bodily fluid or tissue.

10. A method as claimed in claim 1 wherein the $Prp^{Sc}$ is human.

11. A method for typing $Prp^{Sc}$ comprising:

(i) providing a sample containing a $Prp^{Sc}$ protein;

(ii) treating the sample to remove $Cu^{2+}$ and $Zn^{2+}$ from $Prp^{Sc}$ wherein treatment involves treating the sample with a metal chelator or combination of chelators capable of chelating both $Cu^{2+}$ and $Zn^{2+}$;

(iii) subsequently digesting the sample with proteinase K; wherein the digestion products of the sample are compared with one or more standard samples of known $Prp^{Sc}$ type to identify the type in the sample, a difference being indicative of the presence of type 1 or type 2 $Prp^{Sc}$.

12. A method as claimed in claim 11, wherein the metal chelator includes EDTA.

13. A method as claimed in claim 12, wherein the EDTA is present at a concentration of about 15–20 mM.

14. A method as claimed in claim 11, wherein step (ii) involves washing the $Prp^{Sc}$ sample with a buffer.

15. A method as claimed in claim 14, wherein the buffer is a morpholine buffer.

16. A method as claimed in claim 11 wherein the sample comprises any bodily fluid or tissue.

17. A method as claimed in claim 11 wherein the $Prp^{Sc}$ is human.

* * * * *